United States Patent
Lipari et al.

(10) Patent No.: US 8,747,294 B2
(45) Date of Patent: Jun. 10, 2014

(54) ASSAY OF NITRIC OXIDE METABOLITES IN THE CULTURE MEDIA OF HUMAN PREIMPLANTATION EMBRYOS

(75) Inventors: Christopher William Lipari, Jacksonville, FL (US); Annabelle Rodriguez, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 985 days.

(21) Appl. No.: 12/740,800

(22) PCT Filed: Oct. 31, 2008

(86) PCT No.: PCT/US2008/081996
§ 371 (c)(1),
(2), (4) Date: Sep. 24, 2010

(87) PCT Pub. No.: WO2009/059139
PCT Pub. Date: May 7, 2009

(65) Prior Publication Data
US 2011/0009689 A1     Jan. 13, 2011

Related U.S. Application Data

(60) Provisional application No. 61/001,160, filed on Oct. 31, 2007.

(51) Int. Cl.
*A61B 17/43*     (2006.01)
*A61D 7/00*     (2006.01)
*A61B 17/435*     (2006.01)

(52) U.S. Cl.
CPC .................................... *A61B 17/435* (2013.01)
USPC ................. 600/34; 600/33; 600/35; 435/1.1; 435/2; 435/4; 435/7.21; 435/29; 435/430.1; 424/582; 800/21; 423/374; 423/405

(58) Field of Classification Search
USPC ................ 600/33–35; 435/1.1, 2, 4, 7.21, 29, 435/430.1; 424/DIG. 12, 582; 800/21; 423/374, 405
See application file for complete search history.

(56) References Cited

U.S. PATENT DOCUMENTS 6,864,086 B2 *   3/2005   Hansel et al. ................. 435/373

FOREIGN PATENT DOCUMENTS

WO     WO-2005/022149 A1     3/2005

OTHER PUBLICATIONS

Smith et al, detection of urinary tract infections by reduction of nitroblue tetrazolium, Kidney international, vol. 54, pp. 1331.*
Athanassakis, I. et al., "Nitric oxide production by pre-implantation embryos in response to embryotoxic factors," Cell Physiol. Biochem, 2000, 10(3):169-76 (abstract).

(Continued)

*Primary Examiner* — Christine Matthews
*Assistant Examiner* — Sunita Reddy
(74) *Attorney, Agent, or Firm* — Venable LLP; Stefan J. Kirchanski (57) ABSTRACT

The present invention relates, e.g., to a method for predicting the embryonic progression of a preimplantation embryo, comprising measuring in the insemination medium (IM) in which an oocyte was fertilized and subsequently incubated in vitro, thereby generating a pre-implantation embryo, at 18-24 hrs post fertilization, the levels of nitric oxide metabolites (NOx) in the insemination medium (IM), wherein a level of NOx of at least about 1.3 µM indicates that the preimplantation embryo is likely to progress to the blastocyst stage by culture day (CD) 5.

17 Claims, 3 Drawing Sheets

(56) References Cited

OTHER PUBLICATIONS

Battaglia, C., et al., "Embryonic Production of Nitric Oxide and its Role in Implantation: a Pilot Study," J. Assisted Repro. and Genetics, Nov. 2003, 20(11):449-454.

Chen, H-W. et al., "Nitric oxide as a regulator in preimplantation embryo development and apoptosis," Fertility and Sterility, Jun. 2001, 75(6):1163-1171.

Thaler, C.D. et al., "Nitric Oxide in Oocyte Maturation, Ovulation, Fertilization, Cleavage and Implantation: A little dab'll do ya," Current Pharmaceutical Design, 2003, 9, 399-409.

Gouge, R.C. et al., "Nitric Oxide as a Regulator of Embryonic Development," Biology of Reproduction (1998) 58:875-879.

Telfer, J.F. et al., "Identification of nitric oxide synthase in human uterus," Hum. Reprod., Jan. 1995, 10(1):19-23 (abstract).

International Search Report, PCT Application No. PCT/US2008/081996, Apr. 9, 2009.

Extended European Search Report dated Apr. 8, 2011, issued in related European Application No. 088432626.6-2401.

Barroso et al., "Vascular Endothelial Growth Factor, Nitric Oxide, and Leptin Follicular Fluid Levels Correlate Negatively with Embryo Quality in IVF Patients," vol. 72, No. 6, pp. 1024-1026 (1999).

Barrionuevo et al., "Nitric Oxide (NO) and Interleukin-1β (IL-1β) in Follicular Fluid and Their Correlation With Fertilization and Embryo Cleavage," American Journal of Reproductive Immunology, vol. 44, pp. 359-364 (2000).

Lee et al., "Nitric Oxide is Associated with Poor Embryo Quality and Pregnancy Outcome in In Vitro Fertilization Cycles," Fertility and Sterility, vol. 82, No. 1, pp. 126-131 (2004).

Manser et al., "Effect of Inhibiting Nitric Oxide Production on Mouse Preimplantation Embryo Development and Metabolism," Biology of Reproduction, 71, pp. 528-533 (2004).

Tesfaye et al., "The Effect of Nitric Oxide Inhibition and Temporal Expression Patterns of the mRNA and Protein Products of Nitric Oxide Synthase Genes During In Vitro Development of Bovine Preimplantation Embryos," Reprod. Dom. Anim. 41, pp. 501-509 (2006).

McClintock et al., "Higher Urine Nitric Oxide is Associated with Improved Outcomes in Patients with Acute Lung Injury," American Journal of Respiratory and Critical Care Medicine, vol. 175, pp. 256-262 (2007).

"Griess Reagent Kit for Nitrite Determination (G-7921)," Mar. 9, 2003, XP002628406, Retrieved from the Internet: <URL: http://probes.invitrogen.com/media/pis/mp07921.pdf> Retrieved on Mar. 15, 2011.

Gallinelli et al., "Nitric Oxide as an Early Marker of Human Embryo Metabolic Cleavage in ART Using Fresh or Thawed Oocytes," European Journal of Obstetrics & Gynecology and Reproductive Biology, 142, pp. 48-52 (2009).

Lipari et al., "Nitric Oxide Metabolite Production in the Human Preimplantation Embryo and Successful Blastocyst Formation," Fertility and Sterility, vol. 91, No. 4, pp. 1316-1318 (2009).

\* cited by examiner

ASSAY OF NITRIC OXIDE METABOLITES IN THE CULTURE MEDIA OF HUMAN PREIMPLANTATION EMBRYOS

This research was supported in part by a grant from the U.S. National Institutes of Health (NIH RO1 HL075646). The U.S. government thus has certain rights in the invention.

This application is the National Stage application of International Application No. PCT/US2008/081996 filed on Oct. 31, 2008, which claims the benefit of the filing date of U.S. provisional application 61/001,160, filed Oct. 31, 2007, which is incorporated by reference herein in its entirety.

BACKGROUND INFORMATION

In vitro fertilization (IVF) provides infertile couples hope of conceiving in spite of a wide variety of causes for the infertility. The success rates of IVF have continued to rise, accompanied, unfortunately, by a large increase in the risk of multiple pregnancy.

Current protocols include two strategies for minimizing the risk of multiple pregnancy while maximizing the chance of a successful cycle (pregnancy). Established IVF protocols generally include embryo transfer on the third day after fertilization (culture day 3, or CD 3). The best embryos are identified by morphologic criteria, symmetry between the blastomeres, number of blastomeres, and evidence of degeneration of the blastomeres. Unfortunately, morphologic criteria on CD 3 are poorly predictive of the chance of establishing pregnancy. See, e.g., Milki et al (2002) *Fertil Steril* 77, 1191-5; and Rijnders et al. (1998) *Hum Reprod* 13, 2869-73. The number of embryos transferred varies from 1 to 4, based on guidelines published by the American Society for Reproductive Medicine. These guidelines use criteria based on the age of the patient, number of previous successful or unsuccessful attempts, and the quality as assessed by morphologic criteria. Unfortunately this can result in implantation of up to four embryos and high order multiple pregnancy. Another strategy for combating the risk of multiple pregnancy is extended embryo culture in which the embryos are held in culture for five days after oocyte retrieval. The development and commercial availability of sequential embryonic media has made extended embryo culture a potentially useful tool to improve assisted reproductive technologies (ART) efficiency and further reduce multiple births. Papanikolaou et al. *N Engl J Med* 354, 1139-46, in a prospective randomized controlled trial of women under 36 years of age, compared ET of a single cleavage stage embryo (CD 3) with a single blastocyst (CD 5 embryo) and reported a significantly higher rate of pregnancy and delivery in the blastocyst group. The transfer of fewer embryos at the blastocyst stage has the potential to reduce multiple births without compromising the overall pregnancy rate.

One of the major disadvantages of extended culture, however, has been the worry that in approximately 40% of patients, no embryos would be available for transfer in a given cycle. Proponents of extended culture believe that refractory embryos would not be developmentally competent in utero; however, justification for this is lacking and failure to proceed to embryo transfer (ET) subsequent to controlled ovarian hyperstimulation (COH) can have obvious emotional and financial implications. In addition, the possibility of an increased incidence of imprinting errors (Beckwith-Wiedeman syndrome, Angelman syndrome) associated with IVF raises concerns about universal use of extended embryo culture.

Day 5 transfer has the potential for maximizing pregnancy rate but minimizing the multiple pregnancy rate. Day 3 transfer is more cost effective and minimizes the chance that there will be no embryo to transfer. It is apparent that the ability to predict embryonic progression at an earlier stage could potentially influence decisions regarding embryo culture protocols and ET day. There is a need for a quantifiable objective measure of embryonic health, preferably one that reflects metabolic function, which can be used to predict at an early time post insemination/injection if an embryo exhibits high quality and will progress to at least the blastocyst stage.

DETAILED DESCRIPTION

The present inventors have investigated the relationship between NO metabolite levels ($NO_2^-$ and $NO_3^-$, referred to herein together as NOx) generated by preimplantation embryos (e.g., human preimplantation embryos) in culture and the developmental capacity of the embryos. They report herein that a level of at least about 1.3 $\mu M$ NOx in the insemination medium (IM) in which oocytes have been fertilized and incubated in vitro, when measured as early as about 18-30 hours post fertilization, is statistically significantly associated with the ability of the preimplantation embryos to progress to the blastocyst stage by culture day (CD) 5. Embryos that have reached this developmental stage by CD5 are likely to implant properly into a uterus when transferred to a female subject, and pregnancy is likely to ensue. From this observation, the inventors have set forth a method for predicting the embryonic progression of a preimplantation embryo (e.g., for assessing the quality, embryonic health, or developmental competence of the fertilized oocyte or preimplantation embryo; for selecting suitable embryos for implantation; or for diagnosing the chances of pregnancy). The method comprises measuring in the insemination medium (which would otherwise be discarded after the embryos are transferred at about 18-30 hours to cleavage medium) the level of nitric oxide metabolites (NOx), at about 18-30 hours after in vitro fertilization, wherein a level of NOx of at least about 1.3 $\mu M$ indicates that the preimplantation embryo is likely to progress to the blastocyst stage by culture day (CD) 5. Higher levels of NOx (e.g., 2 $\mu M$, 2.5 $\mu M$, 3 $\mu M$, 3.5 $\mu M$, 4 $\mu M$, 4.5 $\mu M$ or even greater) predict an even greater probability that an embryo is like to progress to this stage.

Using a method of the invention, insemination media can be collected on the day after oocyte retrieval, stabilized (e.g., frozen) and analyzed (e.g. sent to a reference laboratory for analysis) for the level of nitric oxide metabolites. Results can be obtained in about 24-48 hours, and the information can be used to identify the embryos with the best chance of establishing pregnancy. A limited number of these high quality embryos can then be transferred on Day 3, resulting in the highest possible chance of pregnancy while minimizing the risk of multiple pregnancy and avoiding the risks of prolonged culture.

A method of the invention has many advantages. For example, it is non-invasive, and provides a quantitative, objective assessment of embryo quality only 18-30 hours after in vitro fertilization. By contrast, conventional methods, such as the subjective morphological assessment of embryos with the use of a microscope, cannot be performed until at least CD 3. Moreover, the inventors show herein that a method of the invention has an even greater predictive power than the current methods, which are generally conducted at least about 48 hours later. The ability to predict embryo quality will impact clinical decisions regarding extended embryo culture and the number of embryos to transfer, and can help reduce the number of multiple births by transferring a reduced number of "high quality" embryos, while at the same time maximizing the chance of a successful pregnancy.

One aspect of the invention is a method for predicting the embryonic progression of a preimplantation embryo, comprising: (a) fertilizing an oocyte (e.g., by in vitro fertilization (IVF-insemination) or intracytoplasmic sperm injection (ICSI), or for embryo transfer for the production of transgenic animals) in insemination medium (IM) (e.g., in about 80 µl of IM) and incubating for about 18-30 hours, thereby generating a preimplantation embryo; and (b) removing the preimplantation embryo to a cleavage medium and determining the level of NO metabolites ($NO_2^-$ and $NO_3^-$, herein referred to as NOx) in the IM left behind, wherein a level of NOx in the IM of at least about 1.3 µM indicates that the preimplantation embryo is likely to progress to the blastocyst stage by culture day (CD) 5. It is noted that in conventional practice, each fertilized oocyte is incubated in about 80 µl of IM, so the µM concentration of described herein is with respect to that volume. If a fertilized oocyte is incubated in a larger or smaller volume of IM, the level (concentration) of the desired NOx value is expected to vary accordingly.

An embryo that is "likely" to progress to the blastocyst stage by CD 5 has about a 70% likelihood progressing to that stage.

The term "about" as used herein means plus or minus 10%. Thus, "about 18 hours" includes a range of 16.2-19.8 hours. For entities that are indivisible, such as oocytes, if "about" that entity is not an integer, it will be evident to a skilled worker that the nearest integer is meant. For example, "about" 8 oocytes means 7-9 oocytes. The endpoints of ranges, as used herein, are included within the range. "About" also means plus or minus 10% when applied to other numbers, such as the % likelihood of an event happening, or the level of NOx. For example, a level of NOx of about 1.3 µM includes 1.2-1.4 µM.

The nitric oxide metabolites may be measured by any of a variety of conventional methods, including a Griess reaction (such as the modified Griess reaction measured by a QuantiChrom™ assay).

In one embodiment of the invention, an embryo that has progressed to the blastocyst stage by culture day (CD) 5 is likely to implant successfully in a female subject and to progress to a pregnancy. An embryo that is "likely" to implant and progress to pregnancy has at least about a 60% likelihood of doing so.

In one embodiment, the preimplantation embryo is human (the oocyte and the sperm are from a human female and male, respectively).

In one embodiment, the method further comprises measuring the number of blastomeres at CD 3, wherein a blastomere number of at least 6 indicates that the embryo is even more likely to progress to at least the blastocyst stage by CD 5.

One embodiment of the invention is a method comprising (a) retrieving a suitable number of oocytes from a superinduced human female (e.g., as many as about 25-30 oocytes, generally between about 10-15); (b) fertilizing the oocytes in vitro (e.g., by IVF or ICSI), e.g., in a volume of about 80 µl of IM, and allowing the oocytes to incubate in the IM for about 18-30 hours, thereby forming preincubation embryos; (c) transferring the preimplantation embryos to cleavage medium and assaying the IM to determine the level of NOx (e.g., by sending the IM to a testing facility); (d) selecting about two preimplantation embryos for which the IM exhibited the highest levels of NOx, of at least about 1.3 µM; and (e) implanting the selected embryos in the uterus of the human female. Other candidate preimplantation oocytes can be stored frozen in case they are needed later for additional implantation.

A method of the invention may be automated (e.g., conducted robotically, and/or miniaturized).

Another aspect of the invention is a kit for predicting the embryonic progression and quality of a preimplantation embryo, comprising a dipstick-based assay that can detect the level of NOx in IM.

Embryos which are assayed by a method of the invention can be used in a variety of assisted reproductive technologies, including in vitro fertilization. In vitro fertilization (IVF) is a process by which oocytes (egg cells, ova) are fertilized by sperm outside of the womb, in vitro. The process involves hormonally controlling the ovulatory process, removing ova from the subject's ovaries and letting sperm fertilize them in an insemination medium. Methods for retrieving oocytes from a subject, inseminating them, and culturing them in IM, followed by a series of cleavage media in vitro, are conventional. Some typical procedures are described in the Examples herein. The fertilized oocyte (zygote, or preimplantation embryo) is then transferred to the subject's uterus, with the intent of establishing a successful pregnancy.

Variants of IVF for which a method of the invention can be used include ICSI (intracytoplasmic sperm injection), a method in which sperm are directly injected into an egg, in vitro. This method can be used when sperm have difficulty penetrating the egg or when sperm numbers are very low.

In one embodiment of the invention, the embryos which are tested are used for generating transgenic animals, a procedure which heretofore has been quite inefficient. In this method, freshly fertilized eggs are harvested before the sperm head has become a pronucleus; the male pronucleus is injected with a transgenic DNA of interest; and once the pronuclei have fused to form a diploid zygote nucleus, the zygote is allowed to divide by mitosis to form a 2-cell embryo. This embryo can then be tested by a method of the invention, and suitable embryos implanted into a suitable foster mother.

Preimplantation embryos for which a method of the invention is used can be generated from a variety of subjects for which in vitro fertilization would be beneficial. Although the exemplary studies herein were carried out with human female patients, it is to be understood that the methods of the invention are applicable to any mammalian female, and can be used to increase the success of, for example, captive breeding programs of endangered species or commercial breeding by IVF of livestock, such as cattle or horses. A method of the invention can be used for a variety of mammals, including pets, farm animals, research animals (mice, rats, rabbits, guinea pigs, rabbits, etc) and primates, including humans.

A variety of types of sterilized insemination medium (IM) can be used in a method of the invention, provided that they allow efficient fertilization of an oocyte by a sperm, in a reasonable period of time. The form of IM used in the Examples, which comprises human tubal fluid (HTF) plus 5% human serum albumin (HSA), is available commercially. A number of other types of IM are also commercially available and will be evident to a skilled worker.

Nitric oxide (NO) is a reactive radical which is oxidized to two primary stable and nonvolatile breakdown products, nitrite ($NO_2^-$) and nitrate ($NO_3^-$). A variety of methods can be used to measure NO levels. One method is to quantitate $NO_2^-/NO_3^-$ as a measure for NO level. In other methods, the nitrate is reduced to form nitrite, and the level of nitrite is then measured. The level of nitrite, then, is indirectly a measure of both of the NO metabolites (referred to herein as NOx), and thus reflects the level of NO in the sample. $NO_2^-$ levels can be measured, e.g., by using the diazotization reaction that was originally described by Griess (the Griess method). Kits to perform this method are available from, e.g., Promega, Madison Wis. Alternatively, one can use the kit which uses a modified Griess method, the QuantiChrom™ Nitric Assay Kit, which is sold by BioAssay Systems, Hayward, Calif. In this method, sulfanylic acid is used to cause a color change, which can then be quantified. Alternatively, the nitrites can be detected fluorometrically or by chemiluminescence. The latter detection method is significantly more sensitive than the former reactions, and can measure in the picomolar range rather than the micromolar range of most Griess reaction-based tests. Another method for measuring nitrate and nitrite is to use an enzyme linked immunosorbent assay (ELISA), e.g, using the Cayman nitrate/nitrate kit (Caymon Chemical company, Ann Arbor Mich.). Other methods for performing the analysis will be evident to a skilled worker. The NOx values discussed herein, and in the claims, were generated with the QuantiChrom™ Nitric Assay Kit, but the values determined by other methods will be comparable.

The NOx levels can be measured at any time between about 18 and 30 hours (e.g., between about 18 and 24 hours). Generally, the most convenient time for making the measurement is about 18 hours after the oocyte has been inseminated/injected (on day 1 after fertilization).

As used herein, the singular forms "a," "an" and "the" include plural referents unless the context clearly dictates otherwise.

A variety of uses for a method of the invention will be evident to a skilled worker. For example, it can be used to increase pregnancy rates with assisted reproductive technologies, to increase the number of embryos available for cryopreservation, or to increase the efficiency of offspring from transgenic intervention.

Methods of the invention can be readily adapted to a high throughput format, using automated (e.g. robotic) systems, which allow many measurements to be carried out simultaneously. Furthermore, the methods can be miniaturized.

The order and numbering of the steps in the methods described herein are not meant to imply that the steps of any method herein must be performed in the order in which the steps are listed or in the order in which the steps are numbered. The steps of any method disclosed herein can be performed in any order which results in a functional method.

Any combination of the materials useful in the disclosed methods can be packaged together as a kit for performing any of the disclosed methods. For example, one embodiment of the invention is a kit which comprises one or more dipsticks for measuring the level of NOx in a culture medium, such as IM. Similar dipstick-based tests exist for detecting nitrites in urine (as evidence of a urinary tract infection). It will be evident to a skilled worker what modifications should be made to such assays. For example, it might be desirable to have a lower limit of sensitivity or a range of colors, since it is likely that the embryos will produce a range of levels. When using a dipstick type assay, an investigator will select the "highest scoring" embryos rather than relying on a specific cut off numerical value for the level of NOx. If desired, defined amounts of positive and negative controls can be included in a kit of the invention. If desired, the reagents (e.g., dipsticks, reagents for development of the detectable signal, etc.) can be packaged in single use form, suitable for carrying one set of analyses.

Kits may supply reagents in pre-measured amounts so as to simplify the performance of the subject methods. Optionally, kits of the invention comprise instructions for performing the method. Other optional elements of a kit of the invention include suitable buffers, enzymes, packaging materials, etc. The kits of the invention may further comprise additional reagents that are necessary for performing the subject methods. The reagents of the kit may be in containers in which they are stable, e.g., in lyophilized form or as stabilized liquids.

In the foregoing and in the following example, all temperatures are set forth in uncorrected degrees Celsius; and, unless otherwise indicated, all parts and percentages are by weight.

EXAMPLES

Example 1

Materials and Methods

A. Study Participants

Subfertile women between 27 and 44 years of age undergoing sonographic-guided transvaginal oocyte aspiration subsequent to COH for the purpose of IVF or intracytoplasmic sperm injection (ICSI) at Johns Hopkins Hospital between Mar. 31 and Jun. 26 of 2006 were included in the study. A single embryologist selected patients for inclusion in a consecutive manner at random time intervals over the course of the study. All patients had undergone standard diagnostic and treatment protocols prior to the initiation of COH. A total of 11 patients produced 79 embryos that were evaluated in this study. Physicians performing the analysis were blinded with regard to the stimulation protocol, infertility diagnosis, embryo morphologic characteristics, embryonic progression and final disposition. This study protocol was approved by the Johns Hopkins Institutional Review Board.

B. Stimulation Protocol

Patients underwent one of three stimulation protocols as determined by age and diagnosis. Briefly, all participants presented on cycle day 2 of the menstrual cycle for a transvaginal ultrasound and serum hormonal measurements. Providing that the serum estradiol ($E_2$) was <60 pg/mL, follicle stimulating hormone (FSH) was <10 mIU/mL and there was no evidence of pelvic pathology or early follicular recruitment, stimulation was initiated under either a gonadotropin releasing hormone (GnRH) agonist (-ag) or antagonist (-an) protocol as prescribed by the treating reproductive endocrinologist.

The GnRH-ag protocol consisted of the daily administration of 1.0 mg of a GnRH-ag subcutaneously (SC) starting 3-7 days following confirmed ovulation on the basis of sonographic and serological data. On cycle day one of the subsequent cycle, the dosage of GnRH-ag was reduced to 0.5 mg daily and continued through to and including the day of oocyte trigger. Patients were started on 225-300 IU of recombinant FSH (Follitropin-α, Gonal-F®; Serono Laboratories, Norwell, Mass., USA) on cycle day 2. Daily human menopausal gonadotropins (Repronex®; Serono Laboratories, Norwell, Mass., USA) were added depending upon the response to stimulation. The dosages of gonadotropins were adjusted in a step-down fashion and decisions regarding such were based on ovarian response, serum $E_2$, and sonographic data.

In the GnRH-an protocol, gonadotropin initiation occurred on cycle day 2 as above, however, this protocol was not preceded by GnRH-ag pituitary downregulation. In contrast, a daily evening dose of ganirelix acetate (Antagon®, Organon, West Orange, Calif., USA) 0.25 mg subcutaneously was administered on the sixth day of stimulation and continued through to and including the day of oocyte trigger.

If patients did not meet initiation criteria due to an elevated serum FSH (>10 mIU/mL), patients were followed until ovulation was confirmed. A single 3 mg subcutaneous dose of a GnRH-an was administered 10 days following the confirmation of ovulation. Cycle day 2 baseline evaluation was repeated and if criteria were met, the GnRH-an protocol noted above was followed.

Dosages were modified by the treating physician based on an evaluation of sonographic and serological data. All patients received a single dose of 10,000 IU of hCG (Profasi, Serono Laboratories, AZ, USA) once three follicles achieved a diameter of at least 18 mm. Ultrasound-guided oocyte retrieval followed 36 hours later.

C. Serum Hormonal Evaluation

Plasma levels of $E_2$ and progesterone (P) were assessed between 7:00 AM and 8:00 AM with an Immulite Automated Analyser (Diagnostic Products Corporation, Los Angeles, Calif.). The intra- and inter-assay coefficients of variation were 6.3%-15.0% and 6.4%-16.0%, respectively for $E_2$ and 5.0%-16.0% and 5.8%-16.0%, respectively for P. The detection limit of the assay was approximately 0.2 ng/mL.

D. Embryo Culture

Following oocyte retrieval, the follicular fluid was examined by the staff embryology team with the assistance of a dissecting microscope (Nikon SMZ 1500) at 15× magnification. Oocytes were removed from the follicular fluid and rinsed with preequilibrated insemination media (IM), which consisted of human tubal fluid (HTF) plus 5% human serum albumin (HSA) (SAGE Biopharma, Bedminster, N.J.). Metaphase II oocytes were subsequently placed in individual 80 µL droplets of IM. Conventional insemination was performed two to four hours later with the addition of 5.0 µL of the processed semen sample containing approximately 15,000 sperm. Seven µL of oil was placed over the sample to prevent evaporative loss. ICSI was performed on 23 of 144 retrieved oocytes as described by Palermo and colleagues (Palermo et al. (1995) *Fertil Steril* 63, 1231-40).

Embryos were cultured at 37° C., 5% $CO_2$ and 21% $O_2$ and reexamined approximately 24 hours following insemination/ICSI for evidence of fertilization. Zygotes were transferred to cleavage media with 5% HSA (SAGE Biopharma, Bedminster, N.J.) and 7.0 µL of oil was placed over the media surface to prevent evaporative loss. Once embryos were transferred to the cleavage media, the IM was collected from each individually cultured embryo and placed in separate 0.2 mL microcentrifuge tubes and stored at −80° C. until processing for NOx measurements. Embryo free media droplets were cultured under identical conditions as the embryos and were used as controls in the NO assays.

Embryos were assessed morphologically on CD 3 and either prepared for ET or placed in blastocyst media with 5% HSA for extended culture to day 5. The decision for a CD 3 ET was based on patient preference following a discussion with the treating physician. Morphological assessment was repeated on CD 5 prior to ET.

Morphological assessment of the cleavage stage embryo on CD 3 consisted of recording the blastomere number and embryo grade as determined by the scoring embryologist. The grading system was modified from that proposed by Veeck and was based on the subjective impression of blastomere uniformity and the degree of cellular fragmentation (L L Veeck An Atlas of human gametes and conceptuses: An illustrated reference for assisted reproductive technology. Parthenon Publishing, New York, 1999). The blastomere number ranged from one to ten and the grade ranged from one to four. A grade one embryo was morphologically poor in quality with non-uniform blastomeres and a high degree of cellular fragmentation, whereas a grade four embryo was characterized by uniform blastomeres and absent or minimal cellular fragmentation. Blastocysts were scored based on the appearance of the inner cell mass as well as the trophectoderm. The system was modified from that proposed by Gardner and colleagues (Gardner et al. In vitro culture of human blastocysts, in Jansen R, Mortimer D, eds. Towards reproductive certainty: infertility and genetics beyond 1999. Camforth: Parthenon Press, 1999: 378-88; Gardner et al. (2000) *Fertil Steril* 73, 1155-58). "A" represented a high quality score marked by minimal fragmentation, whereas a score of "C" was considered poor quality and a score of "B" was neither high nor poor quality.

E. Nitric Oxide Metabolite Assay

Media isolated from cultured embryos or control plates that had been stored in 0.2 mL microcentrifuge tubes at −80° C. were thawed to room temperature. Due to the short half-life of NO, the stable metabolic products (nitrite and nitrate), referred to as NOx, were measured as described by the QuantiChrom™ Nitric Oxide Assay Kit (BioAssay Systems, Hayward Calif., USA), which is an assay based on a modified Greiss reaction with a detection range of 0.1 to 50 µM. The conversion rate from nitrate to nitrite is reported to be greater than 98%. Measurements of NOx in duplicates from each sample were performed as described in the kit protocol. The NOx (µM) was calculated for each of the samples and controls. The difference between the amount of NOx detected in the media that previously contained the embryo and the control media was utilized to describe net NOx gain (production) or loss (embryonic uptake or reduction). Negative values, therefore, indicated that there was a greater amount of NOx in the media alone compared to media that previously contained an embryo.

F. Statistical Analysis

Our main objective was to determine the association of NOx levels in the IM after 24 hours of culture with CD 3 and 5 embryonic development outcomes. To account for non-independence of IM NOx levels in oocytes derived from the same donor, all analyses with IM NOx as the dependent variable used Generalized Estimating Equations regression methods with an exchangeable correlation structure. The average levels of IM NOx in the analysis groups were calculated as linear combinations of the regression coefficients. In order to ensure that there was no heterogeneity by fertilization method, we analyzed whether IM NOx levels differed between embryos fertilized via ICSI and those undergoing conventional IVF treatment. We determined whether IM NOx levels differed by CD 3 morphologic grade (Grades 1-2 vs. Grade 3-4), blastomere number (<6 blastomeres vs. ≥6 blastomeres) and embryo disposition (embryo discarded vs. Transferred/Cryopreserved). Similarly, we determined whether IM NOx levels differed in those embryos that progressed to blastocyst on CD 5 vs. those that did not.

We examined whether IM NOx, blastomere number, or subjective grade were effective in predicting survival of the embryo to CD 5 using simple logistic regression adjusting for clustering of data by donor. We then performed stepwise multiple logistic regression to retain only those predictors that were associated with the odds of survival of the embryo to CD 5 with a significance level of at least p<0.1. This level was chosen to prevent associations that were significant at the borderline from being eliminated during intermediate models of the stepwise procedure. Receiver Operating Characteristic (ROC) curve analysis was performed for predicting survival of the embryo to CD 5 using IM NOx, blastomere number, and subjective grade as classifying variables. The areas under the ROC curves were tabulated with their asymptotic 95% confidence interval. The ROC statistics were compared for each pair of classifying variables. No correction for clustering by donor was applied for ROC analyses. Differences were considered statistically significant at the p<0.05 level.

Example II

Results

In order to evaluate the impact of NOx levels on human embryonic progression and morphologic quality, the IM of embryos was analyzed in a cohort of subfertile women undergoing ovarian stimulation for IVF or ICSI. Patient characteristics, oocyte and embryo dispositions are highlighted in Table 1.

TABLE 1

Patient characteristics, oocyte and embryo dispositions.
Characteristics

| | |
|---|---|
| Age (years) | 34.3 ± 4.6* |
| Subfertility (years) | 3.9 ± 2.7 |
| No. oocytes retrieved | 123 |
| Mean no. oocytes retrieved per patient | 11.2 ± 7.3* |
| No. oocytes inseminated (IVF) | 98 |
| No. oocytes injected (ICSI) | 25 |
| Fertilization rate: IVF (%) | 64/98 (65.3) |
| Fertilization rate: ICSI (%) | 15/25 (60.0) |
| No. Embryos transferred (%) | 22/79 (27.8) |
| No. embryos cryopreserved (%) | 15/79 (19.0) |
| No. embryos discarded (%) | 42/79 (53.2) |
| No. embryos cultured to day five | 52 |
| No. embryos progressing to blastocyst stage by culture day five VA) | 27/52 (51.9) |

*values represent means ± Standard. Deviation (SD)

Eleven patients with a mean age of 34.3 years (range: 27-44 years) underwent COH followed by transvaginal sonographic-guided oocyte aspiration. The duration of subfertility ranged from one to 10 years and was defined as the inability to achieve a pregnancy after one year of regular unprotected intercourse. Two of the 11 patients were excluded from the calculation of subfertility duration secondary to diagnoses of recurrent miscarriage and a history of vasectomy in the spouse. A total of 144 oocytes were obtained, 123 of which were cultured in similar embryonic media. The majority of the oocytes were fertilized by IVF (98/123=80%), with the remaining 20% fertilized by ICSI. Successful fertilization by either method was defined by the presence of two pronuclei at 24 hours as determined by the examining embryologist. Seven samples were not available for analysis due to either media spillage or embryos that were cultured as a group in a single droplet of media. The level of NOx was assessed in the IM of 72 individually cultured embryos with 27 and 45 cultured for 3 or 5 days, respectively. The five day culture resulted in 27 blastocysts, 26 of which had media analyzed 24 hours post insemination/injection.

Figure 1:
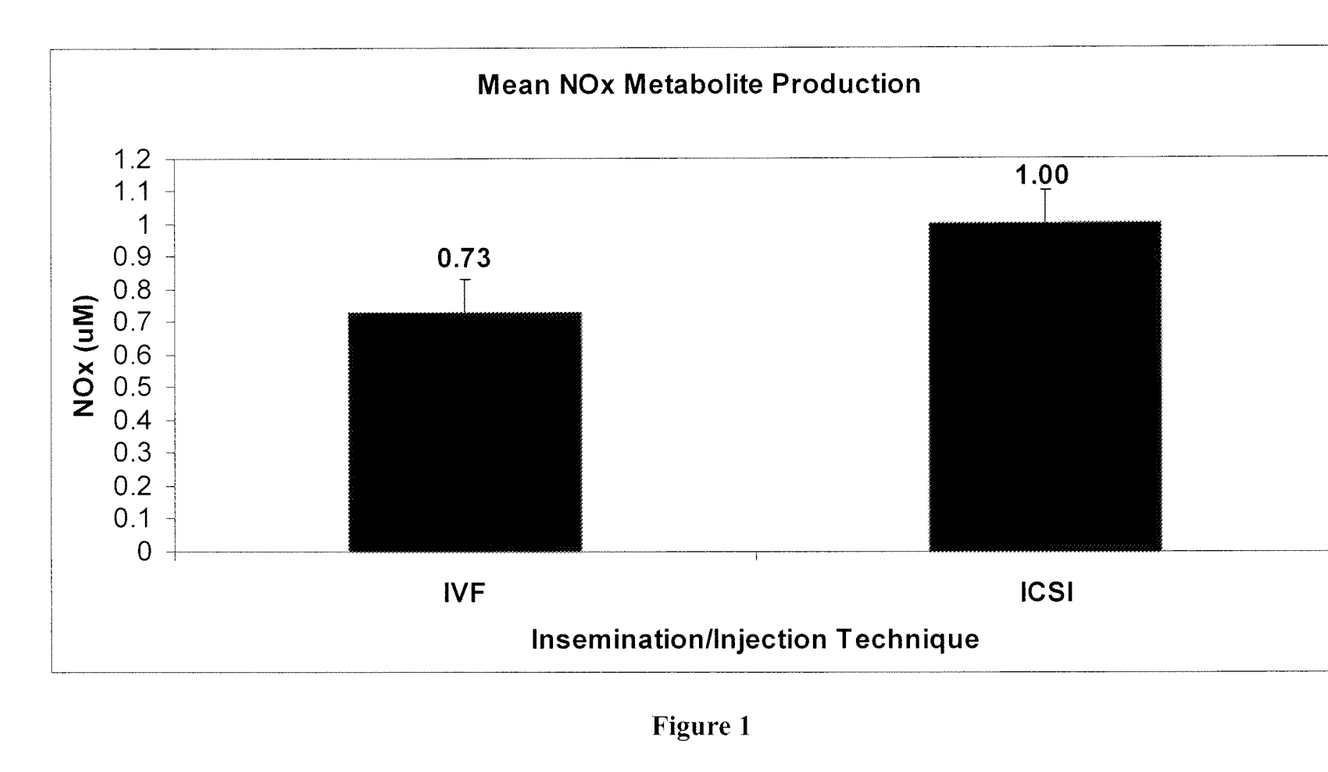
FIG. 1 shows mean NOx metabolite production ($\mu M$) 24 hours post insemination/injection. No statistically significant differences were present between the IVF and ICSI groups (p=0.849).

We first examined whether NOx could be detected 24 hours subsequent to IVF/ICSI in the IM of individually cultured embryos. Conventionally inseminated oocytes (IVF) were compared to those fertilized by ICSI in order to assess the potential contribution of spell a on NOx levels (FIG. 1). No significant differences were noted between IM NOx of embryos fertilized via ICSI (1.00±1.22 µM) and those undergoing conventional IVF treatment (0.73±0.72 µM) (p=0.849). Data were therefore combined for further analysis.

We next examined the relationship between NOx levels and embryo quality. As shown in Table 2, the mean NOx detected in the IM of embryos that possessed fewer than six blastomeres (n=34) on CD 3 was 0.460 µM compared to 1.12 µM in embryos with six or greater blastomeres (n=38), p=0.158. A morphologic grade of 1-2 was associated with a mean NOx of 0.517 µM, whereas a grade of 3-4 was associated with a mean NOx of 0.789 µM, p=0.649. The level of NOx detected in the IM media did approach statistical significance when considering final disposition. The IM NOx produced from embryos that were eventually transferred or cryopreserved was 0.630 µM, compared to embryos that were ultimately discarded, −0.204 µM, p=0.053. The decision to discard was determined by the treating embryologist based on morphologic characteristics as well as a lack of adequate embryonic progression over time.

TABLE 2

Mean IM NO$x$ (µM) 24 hours postinsemination/injection

| Morphologic Grade | | |
|---|---|---|
| Grade 1-2 | Grade 3-4 | p value |
| 0.517 ± 0.826 | 0.789 ± 0.695 | 0.649 |

| Blastomere Number | | |
|---|---|---|
| <6 blastomeres | ≥6 blastomeres | p value |
| 0.459 ± 0.670 | 1.115 ± 0.664 | 0.158 |

| Embryo Disposition* | | |
|---|---|---|
| Transferred/Cryopreserved | Discarded | p value |
| 0.630 ± 0.675 | −0.204 ± 0.719 | 0.053 |

*Values represent mean NO$x$ in µM ± SEM

Figure 2:
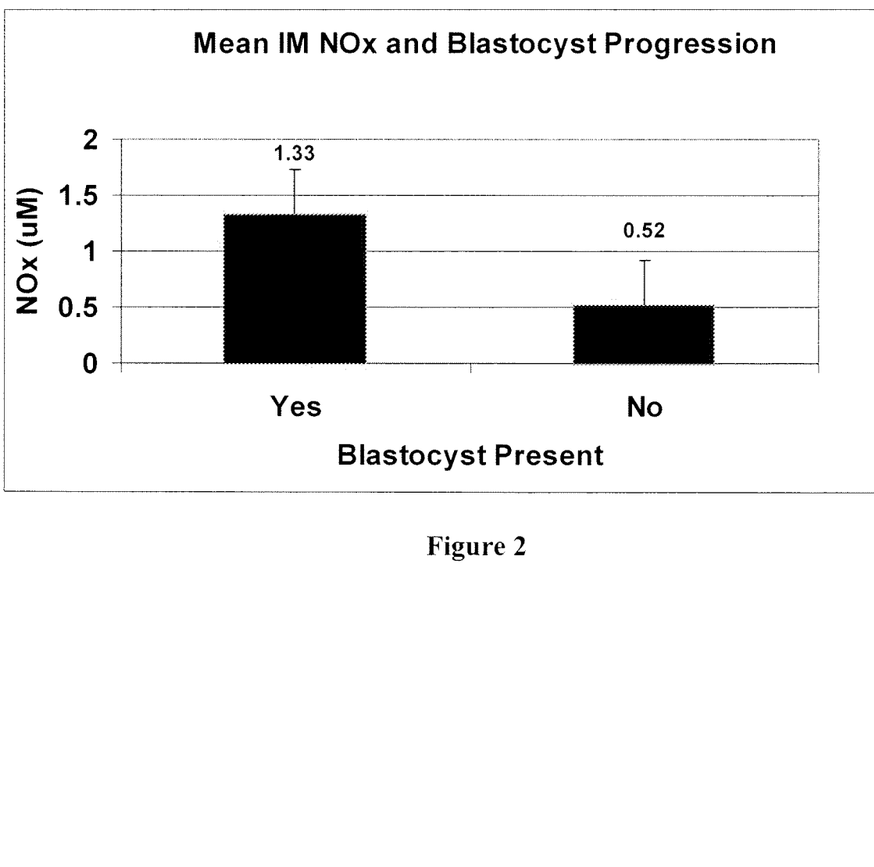
FIG. 2 shows mean NOx metabolite production ($\mu M$) in the IM and the association with progression to the blastocyst stage on CD 5. The differences are statistically significant (p=0/009).

We examined the relationship between NOx levels in the IM and blastocyst progression at CD 5. As shown in FIG. 2, the mean NOx level in the IM was 2.6 times higher in embryos that progressed to blastocysts by CD 5 than those that did not (1.33±0.51 vs. 0.52±0.84 µM, p=0.009). There was no significant difference in IM NOx associated with the morphologic grade of the trophectoderm or inner cell mass in the day five blastocyst (data not shown). There was also no correlation between eventual blastocyst formation and NOx if the embryo culture was extended beyond the fifth day (p=0.982) (data not shown).

While we did not find differences between IM NOx levels, morphologic grade and blastomere number at CD 3, others have shown that embryonic morphology can be of assistance in predicting blastocyst progression on CD 5 (Fisch et al. (2001) Hum Reprod 16, 1970-5). Therefore, given that we found that embryos with higher IM NOx levels progressed compared to embryos with lower IM NOx levels, we used logistic regression and ROC to compare IM NOx levels, morphologic grade and blastomere number as predictors for blastocyst progression. Table 3 displays the odds ratio of blastocyst progression utilizing each parameter as an individual predictor.

TABLE 3

Logistic regression output with regard to blastocyst formation by CD 5: NOx production; blastomere number and morphologic grade

| Individual Parameter | Logistic Regression | | |
|---|---|---|---|
| | OR | 95% CI | p value |
| Grade | 1.42 | 0.54-3.74 | 0.4733 |
| Blastomere No. | 1.34 | 1.15-1.56 | 0.0002* |
| NOx Production | 1.48 | 1.21-1.82 | 0.0002* |
| Multiple Logistic Regression (excluding grade) | | | |
| Model Parameter | OR | 95% CI | p value |
| Blastomere No. | 1.34 | 0.96-1.86 | 0.082 |
| NOx Production | 1.46 | 1.11-1.92 | 0.007* |

*Differences are significantly different p < 0.05

Table 4 explores the potential association further through the tabulation of individual ROC curve results generated by NOx, morphologic grade, and blastomere number. Analysis revealed that only the IM NOx level and CD 3 blastomere number were significantly associated with progression to the blastocyst stage by CD 5 (p<0.02).

TABLE 4

ROC analysis output with regard to blastocyst formation by CD 5: NOx production; blastomere number and morphologic grade

| Parameter | ROC | |
|---|---|---|
| | AUC | 95% CI |
| Grade | 0.51 ± 0.08 | 0.35-0.68 |
| Blastomere No. | 0.70 ± 0.09 | 0.53-0.86 |
| NOx Production | 0.76 ± 0.08 | 0.61-0.90 |

Figure 3:
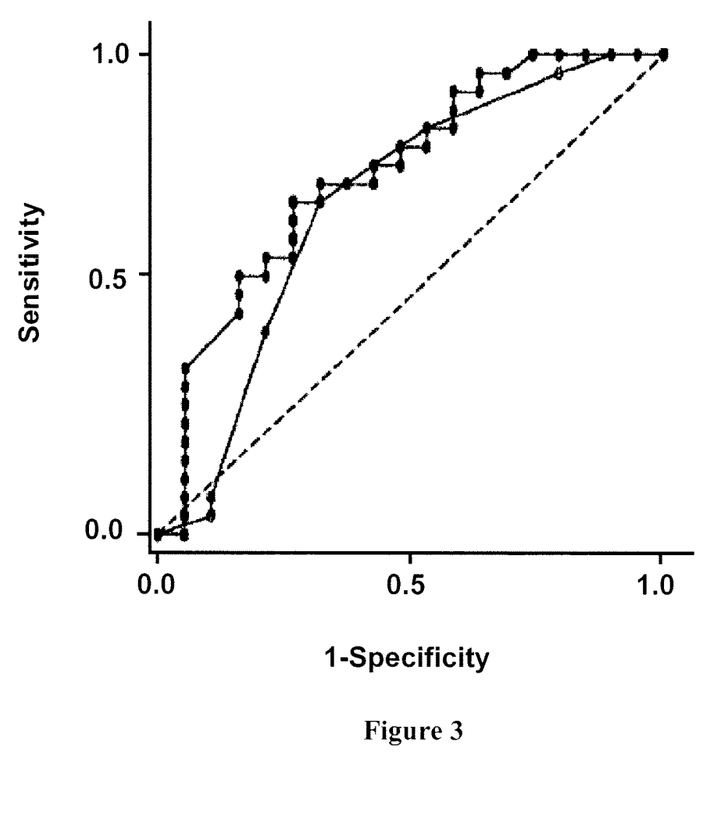
FIG. 3 shows ROC analysis: IM NOx, CD 3 blastomere number and progression to the blastocyst stage by CD 5.—is NOx production ROC area: 0.76;—is Day 3 blastomere number ROC area: 0.70;—is Reference.

Due to the fact that CD 3 morphologic grade was found to have little predictive value, this parameter was omitted from the model utilized to generate the final ROC. FIG. 3 displays the ROC generated from IM NOx and CD 3 blastomere number, highlighting the predictive nature of the two parameters. IM NOx alone revealed a sensitivity of 73.08% with associated specificity of 68.42%, utilizing a cutoff of IM NOx greater than or equal to about 1.33 μM. A CD 3 blastomere number of at least six yielded a sensitivity of 69.23% with associated specificity of 68.42%. Statistical analysis (not shown) revealed that the decision for extended culture to day 5 was not dependent on CD 3 morphology. Although there was no significant difference between the predictive potential of IM NOx and blastomere number on CD 3, a comparison of the curves revealed a trend toward a stronger association of IM NOx with blastocyst formation by CD 5.

Example III

Discussion

This study examined the relationship between NOx levels in the IM media of individually cultured human preimplantation embryos and developmental competence. Individual culture of each embryo provided the ability to measure NOx levels and their relation to embryonic progression and morphologic outcomes. Although the level of IM NOx was not reflective of CD 3 morphology or blastomere number. Importantly, the level of NOx was 2.6 fold higher, a statistically significant difference, in embryos achieving blastocyst formation by CD 5 compared to those failing to reach this stage of development. Furthermore, it appears that when considering CD 3 morphology and NOx, NOx was the strongest predictor of blastocyst formation.

IVF and ICSI fertilized embryos were compared with respect to NOx levels at 18-30 hours culture in order to determine the potential contribution of sperm NOx generation. The level of NOx did not differ according to fertilization technique and hence sperm concentration. These findings are supported by earlier studies showing the inability to detect NOx from spermatozoa. It therefore became apparent that the level of NOx was most likely a reflection of the metabolic activity of the oocyte or zygote. Sperm contributions were considered to be negligible and data gathered from IVF and ICSI techniques were combined.

Since developmental progression in vitro is potentially the best available indicator of embryonic health, short of live birth rate through the transfer of a single embryo, blastocyst progression by CD 5 was utilized as an outcome measure to compare NOx levels. In general, an embryo that has reached the blastocyst stage by CD 5 has at least about a 60% likelihood of resulting in pregnancy. There was a statistically significant association of NOx in the IM media with blastocyst progression. It was also shown that the NOx did not correlate with blastocyst progression if the culture was extended beyond the fifth day. The quality of the blastocyst has been shown to be related to the rate of development, with a significant reduction in pregnancy rate following blastocyst ET if blastocyst formation occurred after CD 5 and 6, correlating reduced embryo quality with slower blastocyst progression (Rodriguez et al. (2000) (Abstract) *Fertil Steril* 74 (Supp. 1): S255-6).

Rodriguez et al. (2000) (supra) proposed a graduated embryo scoring system (GES), based on four sequential observations, to predict blastocyst development from cleavage stage embryos. The highest score tier was associated with a 75% blastocyst progression. Although the GES incorporated additional predictors other than CD 3 morphology and cell number, we compared CD 3 blastomere number and morphologic grade with NOx IM levels. Interestingly, NOx remained the strongest predictor of the three. In fact morphologic grade offered no improvement in the predictive nature of the model. In addition, as mentioned in the literature, inter- and intra-observer variability may complicate this parameter. NOx and CD 3 blastomere number improved blastocyst prediction by CD 5. It should also be noted that IM NOx is a quantitative measurement that can be determined 48 hours prior to the current standard CD 3 morphological assessment or the calculation of a GES, highlighting its utility.

This study has demonstrated that the production of NOx correlates with blastocyst progression, even more so than the standard morphologic criteria. This objective, quantitative measurement obtained early in the developmental process can impact embryo selection at an early stage. This may have a role in embryo selection in countries with governmental restrictions regarding number of embryos cultured, and in conjunction with standard selection criteria, may improve embryonic implantation potential and reduce the multiple birth rate with its known individual and societal burdens.

Example IV

A Randomized, Controlled Prospective Study to Confirm and Extend the Findings in Example II We will do a randomized study of good prognosis patients (those who would have been considered for Day 5 transfer), comparing Day 3 transfer of two embryos selected based on nitric oxide metabolite concentrations (NOx) vs. Day 5 transfer of two embryos selected by the conventional criteria.

Good prognosis IVF patients will be recruited for this study. Patients will be less than 38 years old, have a baseline FSH<10 mIU/mL, and have had less than 2 previous unsuccessful IVF cycles. The study will be presented at the general IVF instructional class prior to initiation of the IVF cycle. Once the controlled ovarian stimulation begins, patients who may be good candidates will be asked to participate. They will have the opportunity to discuss the trial thoroughly as the ovulation induction progresses. Patients who agree to participate will go through the IVF cycle in a completely conventional fashion. If they have at least 8 mature oocytes retrieved, the insemination medium will be collected after the first day of culture. The insemination medium will be assayed for NOx using the modified Greiss reaction as described in Example I. Results of this initial assay will not be available to the patients or the investigators at this point. If the participants have at least 8 normally progressing embryos (≥2 cells on culture day 2), they will be randomized into one of two study groups.

Group 1 will have two embryos transferred on culture day 3 (CD 3). The embryos will be selected for transfer based on the measurement of NOx in the insemination medium recovered on the first day of culture. Embryos with the highest NOx production will be favored. Among embryos with the highest NOx production, embryos with the highest number of blastomeres will be favored.

Group 2 will undergo extended embryo culture and have two embryos transferred on culture day 5 (CD 5). The embryos will be selected for transfer based on the usual morphologic criteria. The trophoblast and inner cell mass are evaluated separately. Embryos with a grade of A for trophoblast and A for inner cell mass will be favored.

Primary outcome measure will be the proportion achieving a clinical pregnancy defined as the presence of fetal cardiac motion on ultrasound four weeks after embryo transfer. Proportions will be compared by Chi-Square. A p-value less than 0.05 will be considered significant. A secondary outcome measure will be the proportion of multiple pregnancy (>1 embryo with fetal cardiac motion on ultrasound four weeks after embryo transfer) and the proportion of higher order multiple pregnancy (>2 viable embryos).

We expect to randomize 250 patients over the course of three years. Participants will only be randomized after they verify that they are indeed good prognosis patients by having at least 8 normally progressing embryos on CD 2. For that reason, the drop-out rate should be minimal. A power calculation indicates that 123 participants per group has 50% power to identify a difference between a pregnancy rate of 30% vs. 40% at the 0.05 level. A preliminary review of the data will be undertaken after the first 100 participants have completed the study and if a significant difference is noted between groups, the study will be terminated unless differences in the secondary outcome measure (multiple pregnancy rate) warrants continuation of the study.

It is expected that this study will confirm and extend the findings of the study summarized in Example II.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above (including U.S. provisional application 61/001,160, filed Oct. 31, 2007) and in the figures, are hereby incorporated in their entirety by reference.

We claim:

1. A method for predicting embryonic progression of a preimplantation embryo, comprising the steps of:
   generating a preimplantation embryo by fertilizing an oocyte and subsequently incubating the fertilized oocyte in vitro in an insemination medium, thereby generating the preimplantation embryo;
   measuring levels of nitric oxide metabolites in the insemination medium (IM) in which the oocyte was fertilized and subsequently incubated in vitro at 18-30 hours post fertilization; and
   determining that the preimplantation embryo will progress to a blastocyst stage by culture day 5 based on whether the levels of nitric oxide metabolites in the insemination medium are at least about 1.3 uM.

2. The method of claim 1, wherein the levels of nitric oxide metabolites are measured about 18 hours post fertilization.

3. The method of claim 2, wherein the preimplantation embryo has been generated by intracytoplasmic sperm injection (ICSI).

4. The method of claim 2, wherein the preimplantation embryo has been generated by introducing a deoxyribonucleic acid sequence of interest into the oocyte, a preliminary step for generating a transgenic animal.

5. The method of claim 2, wherein the nitric oxide metabolites are measured with a Griess reaction.

6. The method of claim 2, wherein the preimplantation embryo which has progressed to the blastocyst stage by culture day 5, is predicted to implant successfully in a female subject and to progress to a pregnancy.

7. The method of claim 2, wherein the preimplantation embryo is human.

8. The method of claim 2, which is automated.

9. The method of claim 1, wherein the preimplantation embryo has been generated by intracytoplasmic sperm injection.

10. The method of claim 1, wherein the preimplantation embryo has been generated by introducing a deoxyribonucleic acid sequence of interest into the oocyte, a preliminary step for generating a transgenic animal.

11. The method of claim 1, wherein the nitric oxide metabolites are measured with a Griess reaction.

12. The method of claim 1, wherein the preimplantation embryo which has progressed to the blastocyst stage by culture day 5 is predicted to implant successfully in a female subject and to progress to a pregnancy.

13. The method of claim 1, wherein the preimplantation embryo is human.

14. The method of claim 1, which is automated.

15. The method of claim 1, further comprising a step of measuring a number of blastomeres at culture day 3, wherein a blastomere number of at least 6 indicates that the embryo will progress to the blastocyst stage by culture day 5.

16. The method of claim 1, wherein the preimplantation embryo is implanted into a uterus of a female mammal on culture day 3 when said embryo has been predicted to progress to the blastocyst stage by culture day 5.

17. A kit for practicing the method of claim 1, comprising one or more dipsticks that can measure nitric oxide metabolites levels and instructions enabling a user to practice the method.

* * * * *